United States Patent
Ji et al.

(10) Patent No.: US 6,355,279 B1
(45) Date of Patent: Mar. 12, 2002

(54) COMPOSITION IMPROVING LIPID METABOLISM

(75) Inventors: Zai-Si Ji; Kazuo Shin; Hiroyuki Ito; Masako Tsunematsu, all of Kanagawa-ken (JP)

(73) Assignee: Meiji Milk Products Company Limited, Tokyo (JP)

( * ) Notice: Subject to any disclaimer, the term of this patent is extended or adjusted under 35 U.S.C. 154(b) by 0 days.

(21) Appl. No.: 09/215,258

(22) Filed: Dec. 18, 1998

(30) Foreign Application Priority Data

Dec. 26, 1997 (JP) .............................................. 9-366768

(51) Int. Cl.[7] .......................... A01N 65/00; A61K 35/78
(52) U.S. Cl. ....................... 424/756; 424/725; 424/752; 424/773
(58) Field of Search ........................... 424/196.1, 195.1, 424/756, 725, 752, 773

(56) References Cited

PUBLICATIONS

Computer Abstract Drugu 94–07755 Kobayashi Et Al "Effect of Leaves of *Ginkgo biloba* on Hair Regrowth in C3H Strain Mice" J. Pharm. Soc Jap 113 No. 10, 718—24 1993.*
Computer Abstract Drugu 96–33908 Juzwiak Et Al "*Ginkgo biloba* extract inhibits the development of experimental atherosclerosis in rabbits" Pol J. Pharmacol 47 suppl. 74 1995.*
Computer Abstract Caplus 1992:28119 (Matsui Et Al "Manufacture of extract with high content of flavonoids from ginkgo leaves" Jap Kokai Tokkyo Koho jp 03227985 Oct. 08, 1991.*
Computer Abstract JICST–EPlus 880006653 Hidenobu Et Al "Acute and subacute toxicity of Shosaiko–to" Oko Yahuri 1987 vol. 33, No. 5 pp 793–808, 1987.*
Computer Abstract JICST–EPlus 950862522 Yujiro Et Al "Toxicological Studies of Kamp Extraxct Preparations." Yakuri to Chiryo 1995 vol. 23, No. suppl 7 1755–1775, 1995.*
PDR for Herbal Medicines Gruenwald Et Al Editor First Edition 1998 Medical Economics Company p. 789 (*Curcuma Zedoaria*) ; 871–2 (*Ginkgo Biloba*), 1998.*
Computer Abstract Frosti AN470431 Ramirez–Tortosa et al "Curcumin ethanol–aqueous extract inhibits in vitro human low denisty lipoprotein lipoperoxidation" Functional Foods: the consumer . . . WyeCollege Apr. 1997.*
Catleman "The Healing Herbs" Pub Rodale Press Tumeric pp. 355–357, 1991.*
Gruenwald Et Al Editors "PDR for Herbal Medicines" PUB 1998 Medical Economics Company, 1997.*
Nakayama Publishing Co., "Arteriosclerosis and Vascular Disorder", *The New Medicine Outline*, 36:16–21, (1991).
Masahiro Yammoto, "Hyperlipemia, Metabolism 26", *Chinese Medicines*, 212–219, (1992).

* cited by examiner

*Primary Examiner*—Herbert J. Lilling
(74) *Attorney, Agent, or Firm*—Browdy and Neimark

(57) ABSTRACT

Extract of at least one selected from GAJUTSU (zedoariae rhizoma), KYOUOU (curcumae rhizoma) and ICHO leaves (ginko leaves) obtained using polar solvent, and composition containing the extract are disclosed; since the extract has an excellent effect on lowering the level of blood triglyceride, is derived from natural material and has an excellent level of safety, the extract and the composition can be used as or in drink, food or medicine.

4 Claims, 3 Drawing Sheets

COMPOSITION IMPROVING LIPID METABOLISM

BACKGROUND OF THE INVENTION

1. Field of the Invention

This invention relates to compositions for improving lipid metabolism in animals including human beings, and more practically relates to compositions containing extract from medicinal plants, which are used in the form of medicine, drink or food. This invention relates, further, to methods for improving lipid metabolism, more practically lowering the level of triglyceride in the blood.

2. Prior Art

In recent years, there has been a steady increase in the number of heart patients suffering from ischemic ailments including angina pectoris and myocardial infarctions, which result from arteriosclerosis, especially coronary arteriosclerosis.

There are numerous factors which are thought to contribute to arteriosclerosis, hyperlipemia, high blood pressure, smoking, stress, diabetes, genetic factors, among others, but the highest risk factor is a high level (i.e. concentration) of lipids in the blood (i.e. hyperlipemia). Hyperlipemia is defined to be the condition in which the levels of both cholesterol and triglycerides (neutral fats) are higher than their normal levels, or the condition in which either of the levels is higher than the normal level; cholesterol and triglyceride are lipid components in blood serum.

When blood serum cholesterol or LDL cholesterol level (concentration) is high, the risk of arteriosclerosis also rises, and when the serum cholesterol level decreases, so does the incidence of coronary arteriosclerosis. It is known that among lipoproteins, LDLs are atherogenic, while HDLs are antiatherogenic. The risk of arteriosclerosis is frequently based solely on the level of HDL cholesterol in the blood, and therefore not enough attention is paid to the level of triglyceride in the blood which is also a clear indication of increased risk or developing arteriosclerosis (The New Medicine Outline, Vol. 36, Arteriosclerosis and Vascular Disorder, p. 20, published by NAKAYAMA Publishing Co. (1991)). In the case of familial hypercholesterolemia, high triglyceride levels increase the risk of both ischemic heart disease and cerebral angiopathy. In the case of critical region hypercholesterolemia, it is well known that the lowering of the level (concentration) of triglyceride is desirable. Therefore any therapy which results in lowering the level of neutral triglyceride in the blood (referred to as "blood triglyceride" hereinafter) is beneficial.

Focusing on this problem, the present inventors focused on a new approach to the prevention and treatment of hyperlipemia, i.e. lowering the risk of arteriosclerosis by lowering the level of blood triglycerides. It is important to note that this is different from, and complementary to, the conventional approach of controlling the level of cholesterol in the blood.

For the medicinal treatment of high blood lipid levels, new highly potent medicines have been developed and evaluated to be effective against familial hypercholesterolemia which had hitherto been refractory; these medicines act by a number of different mechanisms, e.g., absorption inhibition, biosynthesis inhibition and excretion promotion. There are also reports of positive effects resulting from the use of components of Chinese herbal medicines (bupleuri radix, ginseng radix, extractum glycyrrhizae, etc.) as well as various pharmacopoeial (i.e., officially recognized) medicines on lipid metabolism disorders such as hyperlipemia (Masahiro YAMAMOTO, Hyperlipemia, Metabolism 26 (Extra publication: Chinese Medicines): 212–219, 1992).

However, the above-mentioned reference does not mention any of the following: ICHO (ginkgo: Ginkgo biloba) leaves, GAJUTSU (zedoariae rhizoma) the KYOUOU (curcumae rhizoma), nor does it mention lowering the level of blood triglycerides as an approach for therapy.

Generally, it is understood that herbal medicines act on a variety sites and by a variety of mechanisms and metabolisms and that these various actions function collectively to result in effective treatments. Accordingly when new components or Chinese herbal medicines are discovered to be effective against hyperlipemia, these newly discovered components can be expected to be useful and effective when administered alone as well as when administered in combination with herbal medicines or officially recognized medicines.

In consideration of the above, the present inventors intended to find, by screening Chinese herbal medicines, substances capable of improving lipid metabolism and thus lowering the level of blood triglyceride, which could then be used alone or in combination with Chinese herbal medicines or officially recognized medicines.

Further, the present inventors intended to provide the above-mentioned compositions in the form of medicine, drink or food.

SUMMARY OF THE INVENTION

Figure 1:
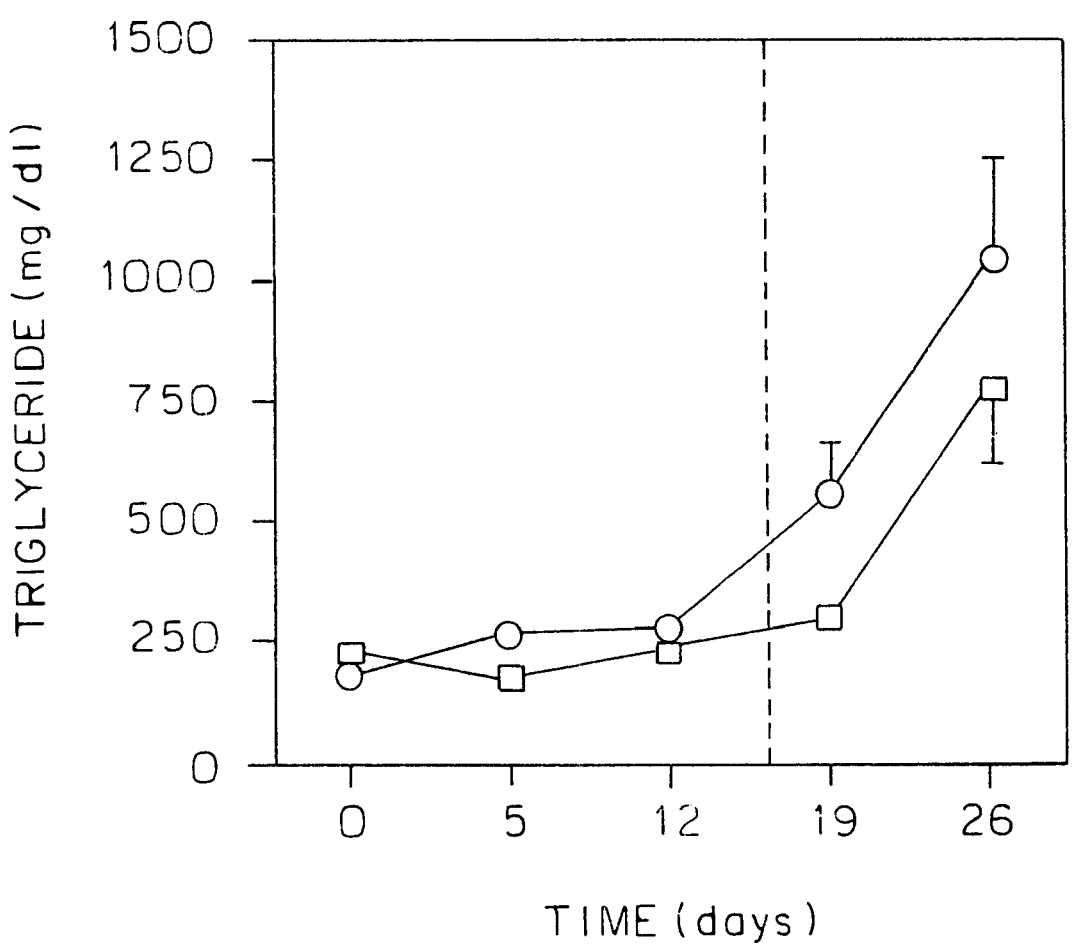
FIG. 1 shows the concentrations of blood triglyceride in test animals (rats) to which the extraction solution from GAJUTSU obtained by extraction with hot water was administered, wherein □ represents said group and ○ represents the rat test group to which the extraction solution was not administered.

In order to attain the above-mentioned intentions, the present inventors have studied intensively various Chinese herbal medicines and as a result found that extracts of ICHO leaves, GAJUTSU and KYOUOU obtained using a polar solvent each have the effect of lowering the level of blood triglyceride, leading to the completion of this invention.

Namely, an object of this invention is to provide lipid metabolism-improving, and more practical blood lipid level lowering, compositions containing, as their effective ingredients, the extracts of these herbal medicines obtained by extraction using a polar solvent. Another object of this invention is to provide methods for improving lipid metabolism, and thereby lowering the level of blood triglyceride by administration of an effective amount of the extract to a patient, either as the thus obtained extract or as a composition containing the extract.

This invention will be explained in detail hereinafter.

DETAILED DESCRIPTION AND EMBODIMENTS OF THE INVENTION

This invention uses at least one member selected from the groups consisting of GAJUTSU, KYOUOU and ICHO leaves. GAJUTSU is the dried rhizome of *Curcuma aeruinosa* Roxb. (*C. zeoaria* non Roxb.) of genus Zingiberaceae which is cultivated in China, Taiwan, etc. GAJUTSU has been used as an aromatic, stomachic, excitant, carminative, anodyne or emmenagogue for indigestion, colic, menopausal disorders, etc. KYOUOU is dried rhizome of *Curcuma longa* L. (*Curmazedoaria Roscoe*) of genus Zingiberaceae which is a perennial native to tropical Asia, cultivated in India, Malaysia, Indonesia, southern China and the southern Kyushu in Japan, etc. KYOUOU has been used as a cholagogue or aromatic stomachic for liver trouble, cholangitis, cholecystolithiasis, catarrhal jaundice, etc., and used as styptic or emmenagogue for hematemesis, blood in the urine, menolipsis, breast pain, stomachache, etc. ICHO leaves are the leaves of the so-called maidenhair tree (ginkgo) and are used as an agent for treating pollakiuria as well as leukorrhea.

This invention involves extracts from ICHO leaves, GAJUTSU, KYOUOU. At least one member selected from the group consisting of INCHO leaves, GAJUTSU and KYOUOU (starting material) is added with or without being cut first into an amount of polar solvent of between 5 and 20 times the amount by weight of the starting material, and then soaked at room temperature for several days at room temperature or at the boiling temperature of the mixture for between ten minutes to several hours, whereby extraction is fulfilled. An example of a polar solvent includes aqueous methanol, aqueous ethanol and water. For example, in the case of extraction using hot water, the starting material is subjected to extraction using hot water (i.e. soaking in hot water) of around 85 to 100° C. or around 100° C. for about 30 to 60 minutes; the resulting mixture may be stirred during the procedure. The extract solution is obtained by filtration, centrifugation or other means. The thus-obtained extract containing solution can be used as is, or as a processed product to be used as an effective ingredient and constitutes the composition of this invention; the processed product includes its concentrate, its paste, its dilution and any product obtained by drying the extraction solution. In the case where the composition of this invention is provided as drink or food, etc. the extraction residue or the product obtained by processing the extraction solution may be used as occasion demands. The extraction solution from which the extraction residue has been removed, the extraction solution containing the extraction residue, and the various products obtained by processing these extraction solutions are referred to as "extract" in this specification, which can be used in this invention.

The extract may be used in combination with the extract of other Chinese herbal medicines or their components(s) which are considered to be effective for improving lipid metabolism disorders.

Such Chinese herbal medicines include SAIKO (bupleurum root: Bupleuri Radix), NINJIN for medicinal use (e.g. Ginseng radix), KANZOU (licorice: Glycyrrhizae Radix), etc.

The extract of this invention has an excellent effect on lowering the level of blood triglyceride, as seen from the data in EXAMPLE 2 below. Accordingly, the extract or the composition of this invention may be used as drink or food, e.g. as a health drink, health food or nutritious food, or may be used as an additive in such drinks and foods, or may be used as a medicine, e.g. a lipid meatabolism-improving agent and an agent for lowering the level of blood triglyceride.

In the case when the composition of this invention is used as or in drink or food, the extract of this invention which is the effective ingredient of the composition of this invention may be used appropriately in the usual manner, as it is or in combination with other drink, food or ingredient(s) therefor. The composition of this invention may employ the form of a solid (powder, granules, etc.), a paste, a solution or a suspension. It is desirable to formulate the composition of this invention as a health drink which is produced by using various ingredients, e.g., sweetening agents, acidifying agents and vitamins for production.

In the case that the composition of this invention is used as or in medicine, the composition containing the extract may be orally administered in various forms, e.g., tablet, capsule, granules, mixed power or syrup. These forms can be made in the usual manners by using the effective ingredient of this invention (i.e. extract) and known adjuvants usually used for the production of medicines, e.g., vehicles, binders, disintegrators, lubricants, corrigents, dissolution adjuvants, suspending agents or coating agents. Although depending on the disease condition, age, body weight, administration procedure, the form of the composition, etc., a dose of the solid extract of this invention is usually about 0.1 mg to about 1,000 mg for an adult.

The effective ingredients of this invention, i.e., the extracts, are derived from natural materials which have been used as Chinese herbal medicines for generations. Therefore, the effective ingredients have either no toxicity or show an extremely low toxicity. Namely, the effective ingredients display an excellent degree of safety; acute toxicity was not observed following oral administration of the effective ingredients, in amounts of 500 mg of extract solution per day in test rats. Accordingly, when the effective ingredients are used in compositions or in drinks or foods the amounts thereof to be used are not specifically limited to drinks or foods for disease prevention or health preservation, but may also be used in ordinary drinks and foods. When the effective ingredients are used in compositions or in medicines, they can be used in the dose range mentioned above, depending on the patient. Since acute toxicity is not observed even at high dosages of any of the effective ingredients, the effective ingredients may be used in amounts exceeding the above-mentioned dose range, as occasion demands.

EXAMPLES

Examples of this invention will be described hereinafter. This invention is not limited by the examples.

Example #1

Preparation of the Extracts

Three herbal medicines, i.e., GAJUTSU, KYOUOU and ICHO leaves were used. Each extraction solution of these herbal medicines was concentrated using an evaporator so that the administration amount of the resultant concentrate, 5 ml/kg, to rats would be 10 times as much as the administration amount to be given to human beings.

Practically, purified water was added to each herbal medicine in an amount equal to 10 times, by weight, the amount of each herbal medicine used and each resulting mixture was subjected to a heated extraction at 100° C. for 45 minutes. Namely, purified water, 960 ml, was added to 95.90 g of GAJUTSU, purified water, 980 ml, was added to 98.06 g of KYOUOU and purified water, 750 ml, was added to 74.46 g of ICHO leaves. After the extraction, each extraction solution was obtained by filtration. Purified water was added to each extraction residue in an amount of 8 times the amount of each extraction results (i.e., purified water, 770 ml for GAJUTSU, 785 ml for KYOUOU and 600 ml for ICHO leaves), and each resulting mixture was subjected to heated extraction at 100° C. for 30 minutes and filtered to give the extraction solutions, which were then combined with the earlier matching extraction solutions. Each resulting mixture was then concentrated using an evaporator to give 800 ml of extraction solution from GAJUTSU, 540 ml of extraction solution from KYOUOU and 250 ml of extraction solution from ICHO leaves.

Example #2

Measurement of Blood Triglyceride

Zucker fatty rats (referred to as "rats" hereinafter) of 5 weeks age were employed as the model animals in this experiment. Zucker fatty rats are thought to be useful pathomodel animals because the pathology thereof—i.e., hyperphagia, corpulence, hyperlipidemia, insulinemia, nearly normal blood sugar levels prior to feeding, slight decrease in sugar-resistibility, etc.—is similar to that of corpulent human beings (Gami UEDA (1979), Hereditary Fatty Rat, Disease Model Animal Handbook, edited by Junichi KAWAMATA and Hiroshi MATSUSHITA, published by ISHIYAKU SHUPPAN Publishing Co., p44–47). The rats were raised on solid feed (CRF1, produced by Charles River, Japan) with a free water supply in a constant-temperature and constant-humidity room (humidity: 60%).

To the rats, an extraction solution of either GAJUTSU, KYOUOU or ICHO leaves obtained in EXAMPLE 1 was administered orally in a dose of 5 ml/kg per rat twice a day for 14 days, and for an additional 14 days in a dose of 10 mg/kg per rat twice a day.

Figure 2:
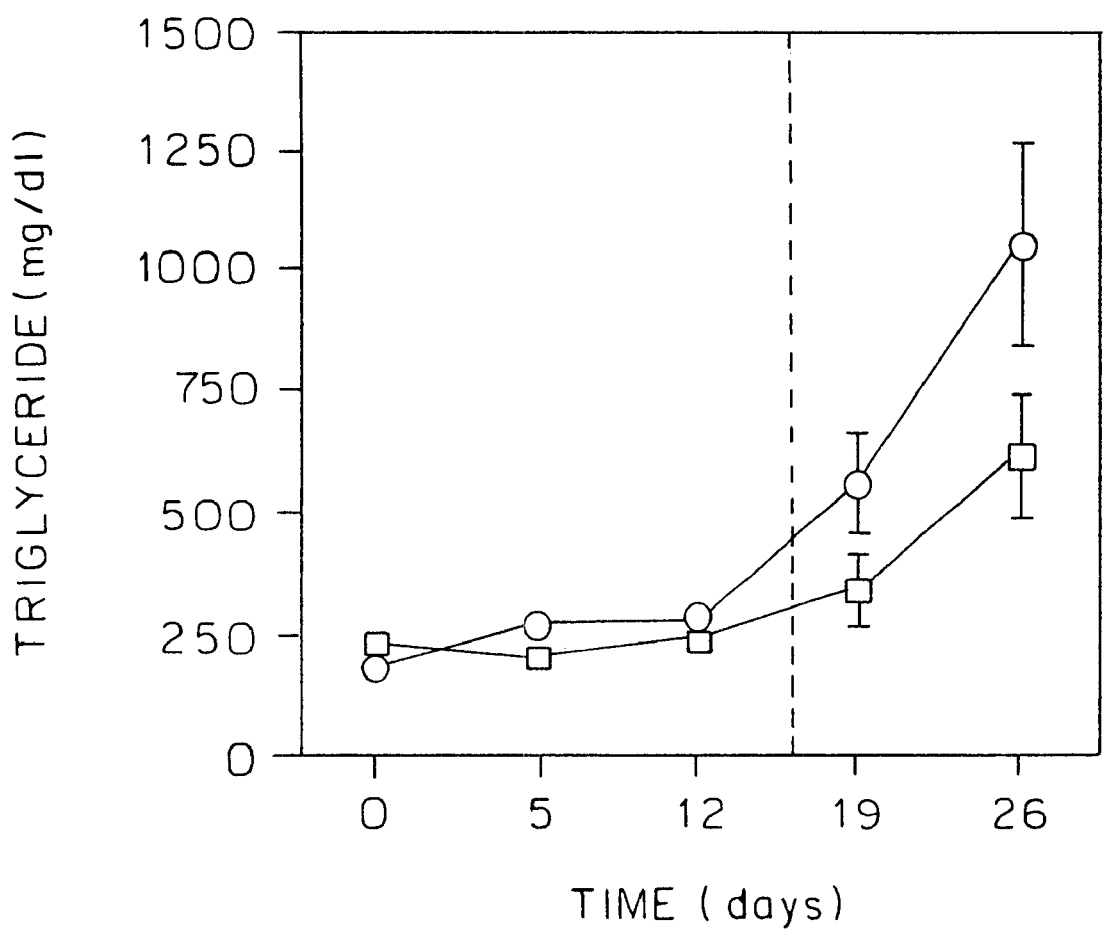
FIG. 2 shows the concentrations of blood triglyceride in test animals (rats) to which the extraction solution from KYOUOU obtained by extraction with hot water was administered, wherein □ represents said group and ○ represents the rat test group to which the extraction solution was not administered.
Figure 3:
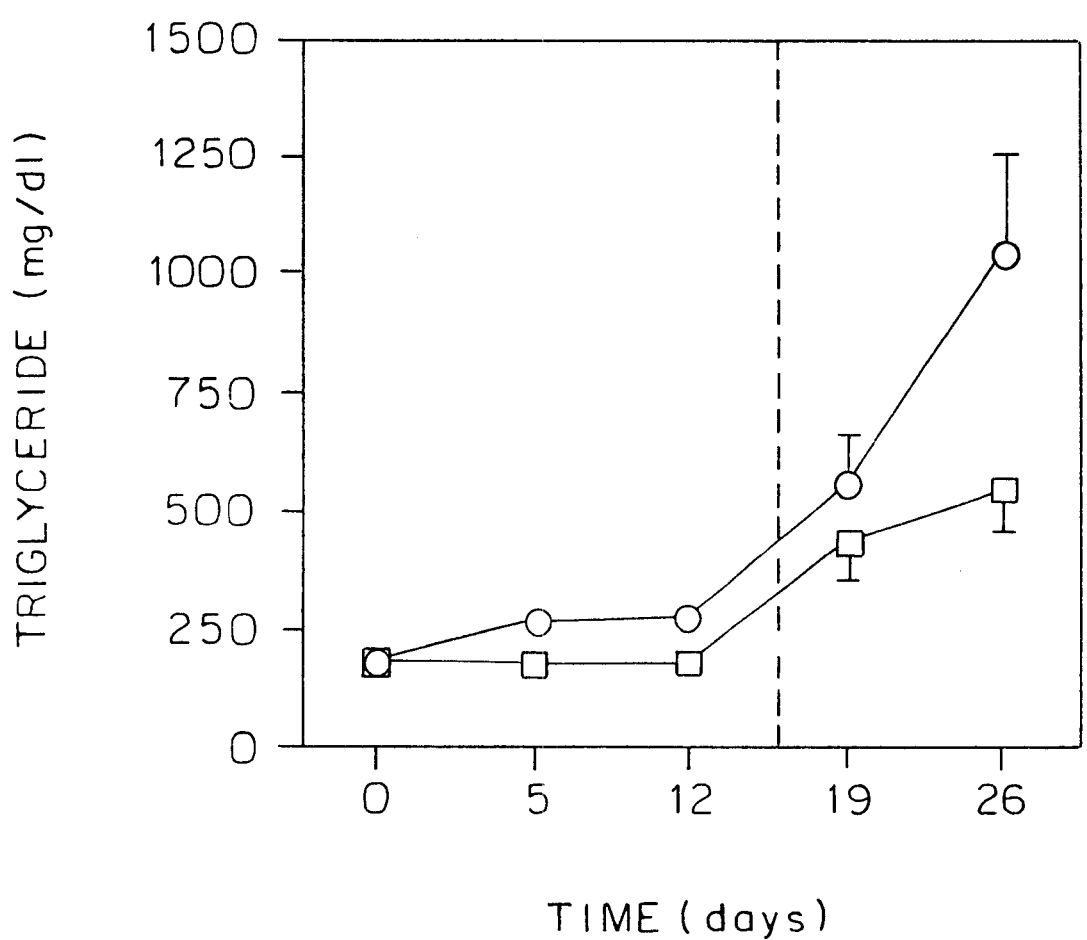
FIG. 3 shows the concentrations of blood triglyceride in test animals (rats) to which the extraction solution from ICHO leaves obtained by extraction with hot water was administered, wherein □ represents said group and ○ represents the rat test group to which the extraction solution was not administered.

5, 12, 19 and 26 days after administration, blood was collected from the orbital vein of each rat. For each sample, the blood serum was separated from the collected blood using a hematocrit and the triglyceride level was then measured using the *Triglyceride G-Test Wako Measurement Kit* (produced by Wako Junyaku Co.). In FIGS. 1, 2 and 3, the measured triglyceride levels (concentrations), as a function of the time following administration, are shown for the groups of rats which received extract solutions of GAJUTSU, KYOUOU and ICHO leaves, respectively.

Results

As seen from FIGS. 1, 2 and 3, which show the effect of promot the decreasing the level of blood triglyceride in the administration of the extraction solution of this invention to the hereditary fatty rats (Zucker Fatty Rats), the levels of blood triglyceride in the rat groups to which the extraction solutions of this invention were given are lower than those in the control groups, i.e., the rat groups to which the extraction solutions were not given. Namely, the extraction solutions of this invention have the effect of lowering the level of blood triglyceride.

Thus, the extracts in this invention prepared from GAJUTSU, KYOUOU and ICHO leaves through extraction using a polar solvent have the effect of lowering the level of blood triglyceride. Therefore, the effect of improving lipid metabolism thereby can be expected, and accordingly, the extracts in this invention are effective in the treatment of hyperlipemia which is the most dangerous factor causing arteriosclerosis. Drinks and foods containing the extracts in this invention are effective in diet therapy for hyperlipemia.

Example 3

Production of Health Drink (1)

To 100 g of the powder obtained by spray-drying the extraction solution of GAJUTSU obtained finally in EXAMPLE 1, 150 g of sugar, 15 g of honey, 1 g of ascorbic acid, 0.5 g of citric acid and appropriate amount of flavoring was added water so that the resulting mixture was 1 kg. The resulting mixture was sterilized at 95° C. for 20 minutes and added into bottles in an amount of 100 mg/bottle under aseptic conditions to give a health drink.

Example 4

Production of Health Drink (2)

To 200 g of the extraction solution of ICHO leaves obtained finally in EXAMPLE 1, 5 g of tocopherol acetate, 10 g of thiamine nitrate, 20 g of nicotinic acid amine, 50 g of anhydrous caffeine, an appropriate amount of benzoate and an appropriate amount of flavoring, was added deionized water so that the resulting mixture was 30 liters. The mixture was sterilized, and added into bottles in an amount of 30 ml/bottle under aseptic conditions to give a health drink for medicinal use.

Example 5

Production of Tablets

| | |
|---|---|
| A: powder obtained by spray-drying the extraction solution obtained finally in EXAMPLE 1 | 50 g |
| B: lactose | 90 g |
| C: corn starch | 29 g |
| D: magnesium stearate | 1 g |

A, B, and C (17 g) were mixed, and granulated together with paste of C (7 g). C (5 g) and D were added to the resulting granules, followed by sufficient mixing. The resulting mixture was subjected to compression in a tableting machine to give 1,000 tablets, each containing 50 mg of A.

What is claimed is:

1. A method for lowering the level of triglyceride in blood, which comprises administering to a person in need thereof an effective amount of a member selected from the group consisting of:

(1) an extraction solution, not containing the resulting extraction residue, of at least one member selected from the group consisting of GAJUTSU (zedoariae rhizoma) and KYOUOU (curcumae rhizoma), obtained by extraction using a polar solvent selected from the group consisting of water;

(2) a dilution of (1);

(3) a concentrate of (1);

(4) a paste of (1); and (5) a dry product of (1).

2. A method for lowering the level of triglyceride in blood, which comprises administering to a person in need thereof an effective amount of a member selected from the group consisting of:

(1) an extraction solution, containing the resulting extraction residue, of at least one member selected from the group consisting of GAJUTSU (zedoariae rhizoma) and KYOUOU (circumae rhizoma), obtained by extraction using a polar solvent selected from the group consisting water;

(2) a dilution of (1);

(3) a concentrate of (1);

(4) a paste of (1); and (5) a dry product of (1).

3. A method according to claim 1, wherein the polar solvent is hot water of 85 to 100° C.

4. A method according to claim 2, wherein the polar solvent is hot water of 85 to 100° C.

* * * * *